(12) United States Patent
Zhang

(10) Patent No.: US 9,049,994 B2
(45) Date of Patent: Jun. 9, 2015

(54) SYSTEM FOR CARDIAC ARRHYTHMIA DETECTION AND CHARACTERIZATION

(75) Inventor: Hongxuan Zhang, Palatine, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 11 days.

(21) Appl. No.: 13/527,639

(22) Filed: Jun. 20, 2012

(65) Prior Publication Data

US 2013/0072806 A1 Mar. 21, 2013

Related U.S. Application Data

(60) Provisional application No. 61/537,138, filed on Sep. 21, 2011.

(51) Int. Cl.
| | |
|---|---|
| *A61B 5/0205* | (2006.01) |
| *A61B 5/021* | (2006.01) |
| *A61B 5/00* | (2006.01) |
| *A61B 5/029* | (2006.01) |
| *A61B 5/0452* | (2006.01) |

(52) U.S. Cl.
CPC ........... *A61B 5/02108* (2013.01); *A61B 5/0205* (2013.01); *A61B 5/7264* (2013.01); *A61B 5/029* (2013.01); *A61B 5/0452* (2013.01)

(58) Field of Classification Search
USPC ................. 600/481, 483, 485, 508–509, 513, 600/515–519
IPC ........... A61B 5/04,5/02, 5/00, 5/72, 5/74; G06F 19/3418, 19/345; A61N 1/36, 1/3702; G06K 9/00523; A61M 2205/18, 2230/30
See application file for complete search history.

(56) References Cited

U.S. PATENT DOCUMENTS

| | | | |
|---|---|---|---|
| 6,485,429 B2 | 11/2002 | Forstner | |
| 6,496,732 B1 | 12/2002 | Wallace | |
| 6,511,438 B2 | 1/2003 | Bernstein et al. | |
| 6,561,986 B2 | 5/2003 | Baura et al. | |
| 6,623,434 B2 | 9/2003 | Chesney et al. | |
| 6,636,754 B1 | 10/2003 | Baura et al. | |
| 6,754,530 B2 | 6/2004 | Bakels et al. | |
| 6,758,822 B2 | 7/2004 | Romano | |
| 6,829,501 B2 | 12/2004 | Nielsen et al. | |
| 6,908,438 B2 | 6/2005 | Orr et al. | |
| 6,929,610 B2 | 8/2005 | Forstner | |
| 6,975,903 B1 | 12/2005 | Min et al. | |
| 7,018,340 B2 | 3/2006 | Jaffe et al. | |
| 7,024,244 B2 | 4/2006 | Muhlenberg et al. | |
| 7,070,569 B2 | 7/2006 | Heinonen et al. | |
| 7,226,418 B2* | 6/2007 | Kim ............................. | 600/485 |
| 7,251,524 B1 | 7/2007 | Hepp et al. | |

(Continued)

*Primary Examiner* — Deborah Malamud

(57) ABSTRACT

A system for heart performance characterization and abnormality detection comprises an input processor and at least one signal processor. The input processor receives, sampled data representing a patient blood pressure signal and a concurrently acquired electrocardiogram (ECG) signal representing heart electrical activity of the patient. The at least one signal processor, synchronizes the patient blood pressure signal and the heart electrical activity signal, identifies at least two points of a heart electrical activity signal cycle, integrates signal data values representing the amplitude of the patient blood pressure signal of a segment between the identified two points to derive an integral value over time duration of the segment representing an area under the blood pressure signal waveform between the identified two points and in response to the derived integral value, initiates generation of a message associated with a medical condition of the patient.

18 Claims, 11 Drawing Sheets

(56) References Cited

U.S. PATENT DOCUMENTS

| | | |
|---|---|---|
| 7,344,497 B2 | 3/2008 | Kline |
| 7,367,954 B2 | 5/2008 | Starr et al. |
| 7,467,005 B2 | 12/2008 | Schmid et al. |
| 7,493,164 B1 * | 2/2009 | Koh .................................. 607/23 |
| 7,563,231 B2 | 7/2009 | Bhunia |
| 7,608,045 B2 | 10/2009 | Mills |
| 7,611,470 B2 | 11/2009 | Rubinstein et al. |
| 7,615,011 B2 | 11/2009 | Sugo et al. |
| 7,704,209 B2 | 4/2010 | Bennett et al. |
| 7,876,251 B2 | 1/2011 | Zhang |
| 2003/0013980 A1 | 1/2003 | Starr et al. |
| 2004/0118402 A1 | 6/2004 | Heinonen |
| 2005/0090753 A1 | 4/2005 | Goor et al. |
| 2009/0259266 A1 | 10/2009 | Zhang et al. |
| 2010/0016735 A1 | 1/2010 | Harpas et al. |
| 2010/0042007 A1 | 2/2010 | Blanco et al. |
| 2010/0076326 A1 | 3/2010 | Cohen et al. |
| 2010/0099992 A1 | 4/2010 | Holschneider et al. |
| 2010/0152598 A1 | 6/2010 | Zhang |
| 2010/0179421 A1 | 7/2010 | Tupin |
| 2010/0268518 A1 | 10/2010 | Sugo |
| 2011/0028856 A1 | 2/2011 | Zhang |
| 2011/0166618 A1 | 7/2011 | Zhang |
| 2011/0282227 A1 | 11/2011 | Zhang |
| 2012/0136264 A1 | 5/2012 | Zhang |

\* cited by examiner

FIGURE 4

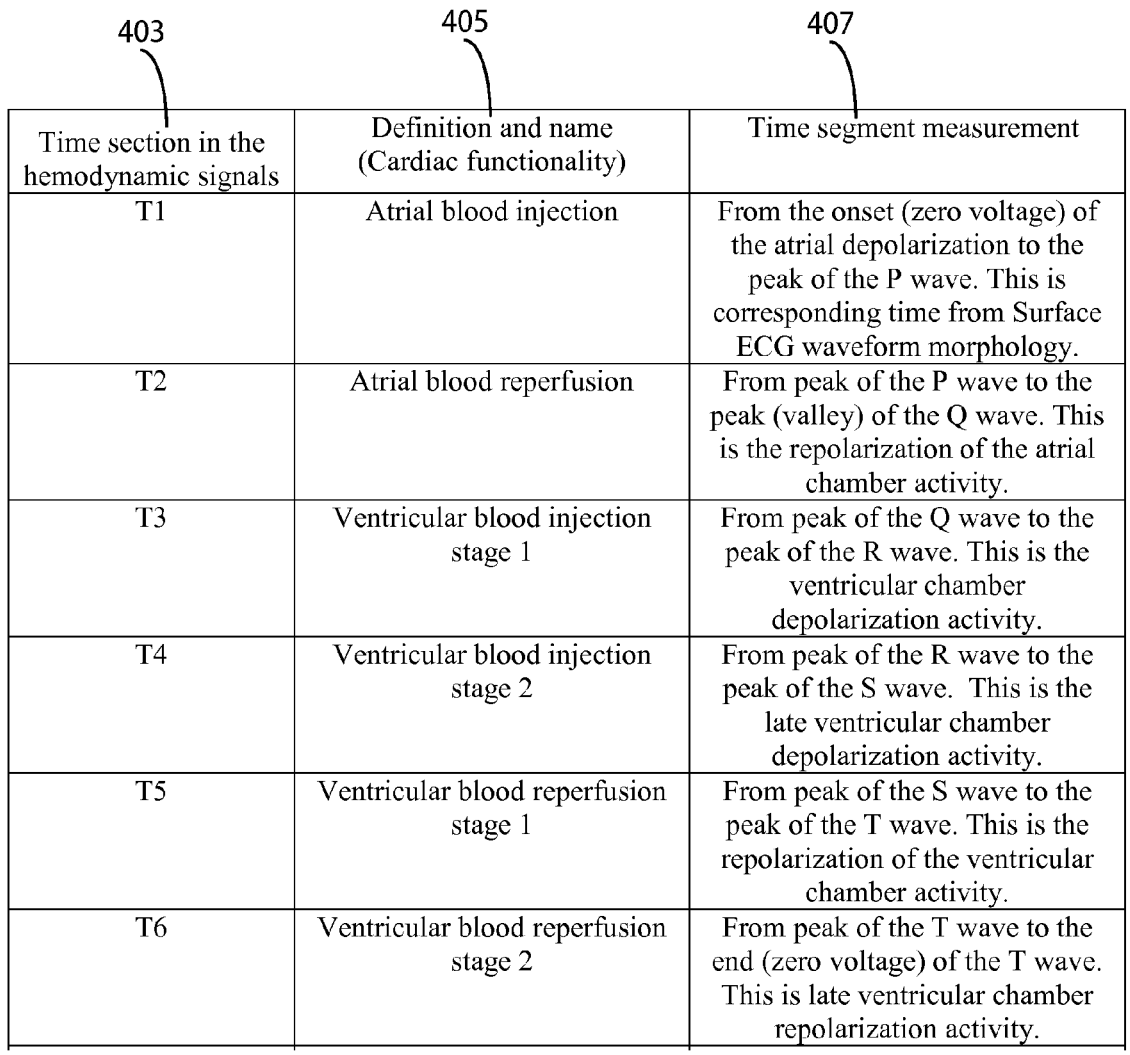

| Time section in the hemodynamic signals | Definition and name (Cardiac functionality) | Time segment measurement |
|---|---|---|
| T1 | Atrial blood injection | From the onset (zero voltage) of the atrial depolarization to the peak of the P wave. This is corresponding time from Surface ECG waveform morphology. |
| T2 | Atrial blood reperfusion | From peak of the P wave to the peak (valley) of the Q wave. This is the repolarization of the atrial chamber activity. |
| T3 | Ventricular blood injection stage 1 | From peak of the Q wave to the peak of the R wave. This is the ventricular chamber depolarization activity. |
| T4 | Ventricular blood injection stage 2 | From peak of the R wave to the peak of the S wave. This is the late ventricular chamber depolarization activity. |
| T5 | Ventricular blood reperfusion stage 1 | From peak of the S wave to the peak of the T wave. This is the repolarization of the ventricular chamber activity. |
| T6 | Ventricular blood reperfusion stage 2 | From peak of the T wave to the end (zero voltage) of the T wave. This is late ventricular chamber repolarization activity. |

FIGURE 5

| Area segmentation in the hemodynamic signals or other blood signal waveform 503 | functions 505 |
|---|---|
| S1 | Atrial blood injection volume and energy |
| S2 | Atrial blood reperfusion volume and energy |
| S3 | Ventricular blood injection stage 1 volume and energy |
| S4 | Ventricular blood injection stage 2 volume and energy |
| S5 | Ventricular blood reperfusion stage 1 volume and energy |
| S6 | Ventricular blood reperfusion stage 2 volume and energy |

Figure 6

| Area segmentation in the hemodynamic signals or other blood signal waveform | functions |
|---|---|
| S1, S2, S3, S4, S5, S6,.... | Uni-section or uni-cardiac-procedure chamber blood output volume and index; these parameters are used to track chamber hemodynamic response and activity in each heart cycle and to diagnose variation and variability of these sections; |
| $Hemo\_Ratio_{Atrial_{ij}} = \dfrac{S_i}{S_j}$<br>i, j ∈ atrial function section | Atrial cross cardiac chamber blood output ratio, indicating the blood injection and reperfusion volume and energy proportion; |
| $Hemo\_Ratio_{Ventricular_{ij}} = \dfrac{S_i}{S_j}$<br>i, j ∈ ventricular function section | Ventricular cross cardiac chamber blood output ratio, indicating the blood injection and reperfusion volume and energy proportion; |
| $Hemo\_Ratio_{Atrial-Ventricular_{ij}} = \dfrac{S_i}{S_j}$<br>i ∈ atrial function section, and<br>j ∈ ventricular function section | Atrial to Ventricular mutual cardiac chamber blood output ratio, indicating the blood injection and reperfusion volume and energy proportion between atrial and ventricular chambers; |

603 — Area segmentation column
605 — functions column

SYSTEM FOR CARDIAC ARRHYTHMIA DETECTION AND CHARACTERIZATION

This is a non-provisional application of provisional application Ser. No. 61/537,138 filed Sep. 21, 2011, by H. Zhang.

FIELD OF THE INVENTION

This invention concerns a system for heart performance characterization and abnormality detection by deriving a parameter value representing an area under a blood pressure signal amplitude waveform of an identified segment of the waveform.

BACKGROUND OF THE INVENTION

Heart chamber (such as atrium and ventricle) hemodynamic blood output is used to diagnose and characterize heart arrhythmias and pathologies, such as atrial fibrillation and left ventricle myocardial ischemia. Chamber blood output is a measure of the blood ejected by a cardiac chamber, such as a left ventricle in one minute or in one heart beat, and is an important vital sign for patient cardiac function and health status monitoring. There are different methods used to calculate chamber blood output, such as calculation and characterization based on a blood pressure waveform, thermodilution, bio-impedance, pulse contour and ultrasound method, for example. However most of these clinical methods are invasive and not reliable and have application limitations including complexity, timing problems, sensitivity and generation of false alarms, for example.

The cardiovascular system comprises, a pump—the heart, a carrier fluid—blood, a distribution system—the arteries, an exchange system—the capillary network, and a collecting system—the venous system. Blood pressure is the driving force that propels blood along the distribution network. Chamber blood ejection volume is the volume of blood pumped by the right and left atrium and ventricle of the heart in one contraction. Specifically, cardiac output comprises volume of blood ejected from ventricles during a systole phase. The blood ejection volume is not all of the blood contained in the cardiac chamber. Normally, only about two-thirds of the blood in the cardiac chamber is put out with each beat. What blood is actually pumped from the cardiac chamber is the chamber blood flow volume and it, together with the heart rate, determines the chamber blood output. There is a lack of efficient and low cost known external non-invasive measuring, estimation and calculation systems using NIBP (non-invasive blood pressure) and ECG signals for cardiac chamber blood flow output and volume determination, especially for emergencies.

Accurate hemodynamic measurement and parameter calculation, is needed to monitor and characterize patient health status. Accuracy of known chamber blood calculation of CO (cardiac output) and SV (stroke volume) for a left ventricle is typically impaired due to blood pressure measurement in a noisy environment, or measurements derived using image scanning and acquisition with imprecise timing. Additionally, known systems are typically based on invasive signal acquisition and data measurements and fail to provide accurate chamber blood output analysis and health parameter calculation. Such known systems involve need for, blood samples for Fick cardiac output measurement, images of EoD (end of diastolic) and EoS (end of systolic) phases in angiographic procedures for cardiac output calculation, and deviation of measurement data in thermodilution based cardiac output monitoring, for example. Known less-invasive or non-invasive methods for chamber blood output estimation attempt to utilize blood stroke volume within local vessels to proportionally estimate the heart SV (stroke volume). The nonlinear relationship between measurement and actual heart chamber blood output may result in substantial calculation errors and false alarms in monitoring, especially in critical care monitoring and lead to inaccurate diagnosis.

Known hemodynamic signal analysis, such as cardiac output and stroke volume estimation, usually utilizes one chamber output, such as left ventricular CO, to estimate the cardiac function. Known systems typically fail to use multi-chamber blood output data for determination of cardiac arrhythmias and pathology, for example. A system according to invention principles addresses these deficiencies and related problems.

SUMMARY OF THE INVENTION

A system detects and characterizes cardiac arrhythmias and malfunctions by using non-invasive hemodynamic signals, such as non-invasive blood pressure data and SPO2 data to calculate chamber blood flow parameters and chamber function ratios to detect and analyze heart function and blood flow characteristics, such as atrial fibrillation and myocardial ischemia severity. A system for heart performance characterization and abnormality detection comprises an input processor and at least one signal processor. The input processor receives, sampled data representing a patient blood pressure signal and a concurrently acquired electrocardiogram (ECG) signal representing heart electrical activity of the patient. The at least one signal processor, synchronizes the patient blood pressure signal and the heart electrical activity signal, identifies at least two points of a heart electrical activity signal cycle and in response to a parameter value representing an area under the blood pressure signal amplitude waveform of a segment between the identified two points, initiates generation of a message associated with a medical condition of said patient

BRIEF DESCRIPTION OF THE DRAWING

FIG. 4 shows a Table indicating segmented signal portions in a hemodynamic signal waveform, according to invention principles.

FIG. 5 shows a Table indicating segmented signal areas in a hemodynamic signal and waveform, according to invention principles.

FIG. 6 shows a Table showing calculated parameters for chamber output and arrhythmia diagnosis, according to invention principles.

DETAILED DESCRIPTION OF THE INVENTION

Figure 1:
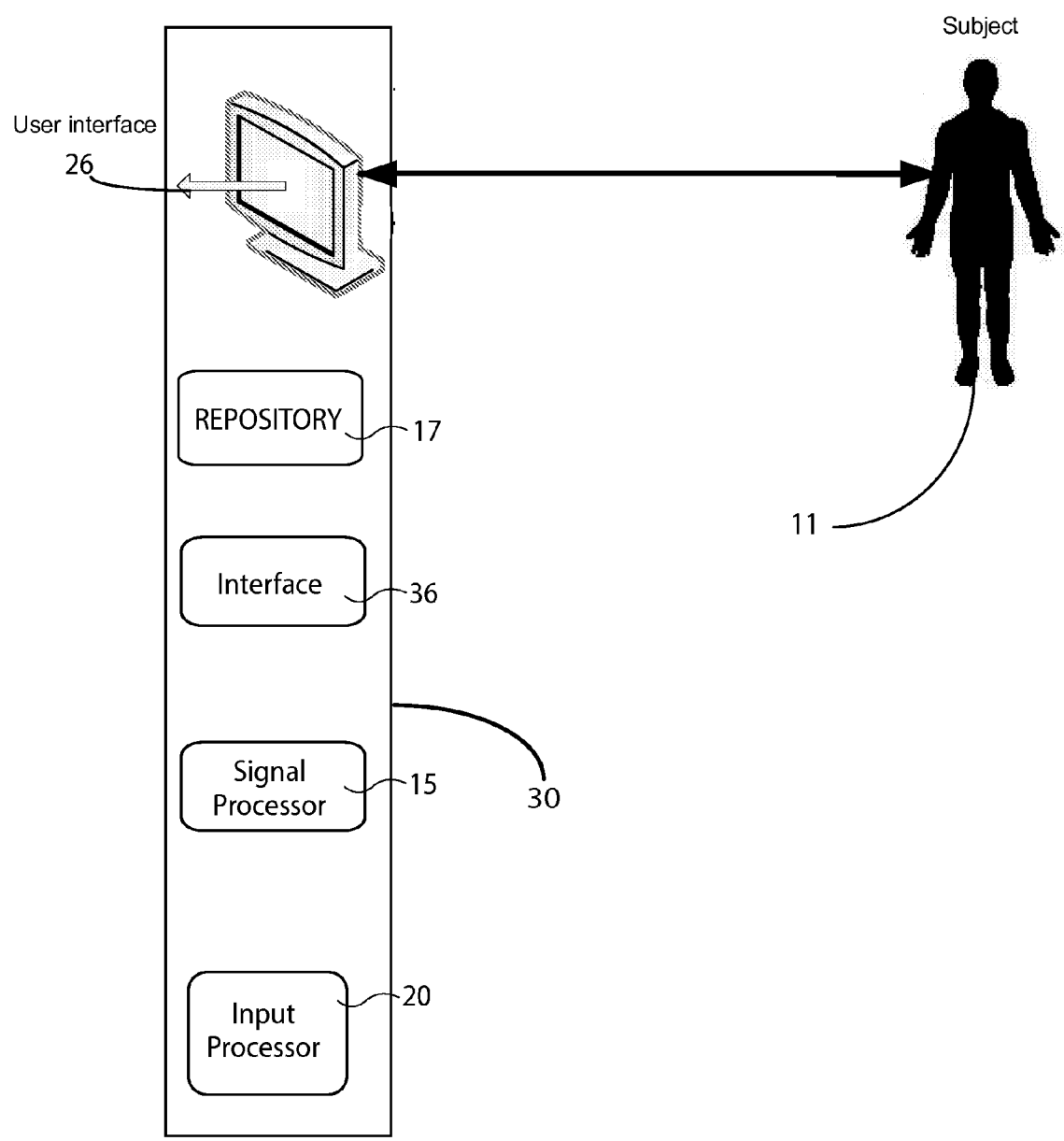
FIG. 1 shows a system for heart performance characterization and abnormality detection, according to invention principles.

A system detects and characterizes cardiac arrhythmias and malfunctions by using non-invasive hemodynamic signals, such as non-invasive blood pressure data and SPO2 data and waveforms, to analyze and diagnose blood flow quantitatively. The system calculates chamber blood flow parameters and ratios to detect and analyze heart function and blood flow characteristics of conditions including atrial fibrillation and myocardial ischemia as well as their severity and trend. The system calculates parameters associating non-invasive hemodynamic signals with a chamber cardiac pump. The signals may include an ultrasound waveform, an image blood flow mapping signal or a signal from an NIBP device or a finger tip blood flow pulse device. The system uses quantitative statistical calculation providing synchronized chamber signal parameters including a variability indication, for example, for improving stability, especially in noisy conditions. The system supports cardiac tissue and hemodynamic function monitoring, diagnosis and evaluation, by identifying cardiac disorders, differentiating between cardiac arrhythmias, characterizing pathological severity, predicting life-threatening events, and evaluating effects of drug delivery.

The system acquires and categorizes synchronized hemodynamic signals associated with different heart chambers and derives a chamber based blood output ratio and related parameters for early stage myocardial ischemia detection, for example. The system provides advantageous functions to calculate to quantitatively and qualitatively determine patient cardiac health status using gated, categorized and synchronized hemodynamic blood signal waveforms from different heart chambers.

In a CCU (critical care unit) and ICU (intensive care unit), vital sign signals (such as ECG, SPO2 and NIBP signals) are usually used for patient monitoring and health status diagnosis and characterization. Vital sign signals have a close relationship with hemodynamic signals. The system advantageously synchronizes and combines use of electrophysiological signals, such as ECG signals, with hemodynamic signals, such as NIBP signals from different locations of the body (arm, neck, wrist, for example), to determine blood flow and activity in each cardiac chamber. The system advantageously uses electrophysiological signals (such as intra-cardiac signals and surface ECG signals) to gate and extract particular signal portions of hemodynamic signals for cardiac function analysis.

Hemodynamic signals, including non-invasive and least invasive blood pressure signals (such as blood pressure signals, SPO2 signals, for example) together with related blood pressure waveform derived parameters (such as rate of blood pressure change dP/dt, a time domain parameter, a frequency domain parameter, statistical parameter, for example), are utilized to quantitatively characterize heart function, arrhythmias, and patient health status. In addition to using cardiac electrophysiological signals, such as surface ECG signals or intra-cardiac electrograms, the system combines multiple hemodynamic and electrophysiological parameters and ratios to derive quantified results and identify abnormal event timing, arrhythmia location and pathology severity, for example. The hemodynamic signals include, a non-invasive or least invasive blood pressure from different parts of a human body, blood related signals, such as an SPO2 signal, capnograph signals, blood oxygen saturation ratios, for example and derived hemodynamic parameters, such as dP/dt, volume and flow speed, for example.

FIG. 1 shows system 10 for heart performance characterization and abnormality detection. Server 30 includes user interface 26, signal processor 15, input processor 20 and repository 17. User interface 26 comprises a graphical user interface (GUI) presented on a display together with a keyboard, mouse, touchscreen or voice recognition device, for example, for user data and command entry into system 10. Patient monitoring signals including ECG, ICEG, blood pressure, SPO2 and other vital sign signals, are acquired from patient 11 buffered, filtered, amplified, digitized and processed by interface 36 for display on user interface 26.

Input processor 20 receives, sampled data representing a patient blood pressure signal and a concurrently acquired electrocardiogram (ECG) signal representing heart electrical activity of the patient. At least one signal processor 15, synchronizes the patient blood pressure signal and the heart electrical activity signal, identifies at least two points of a heart electrical activity signal cycle, integrates signal data values representing the amplitude of the patient blood pressure signal of a segment between the identified two points to derive an integral value over time duration of the segment representing an area under the blood pressure signal waveform between the identified two points. Processor 15, in response to the derived integral value, initiates generation of a message associated with a medical condition of the patient. Repository 17 stores the patient blood pressure signal and the electrocardiogram (ECG) signal, determined parameters, mapping information that associates ranges of the derived integral values or values derived from the derived integral values with corresponding medical conditions.

Figure 2:
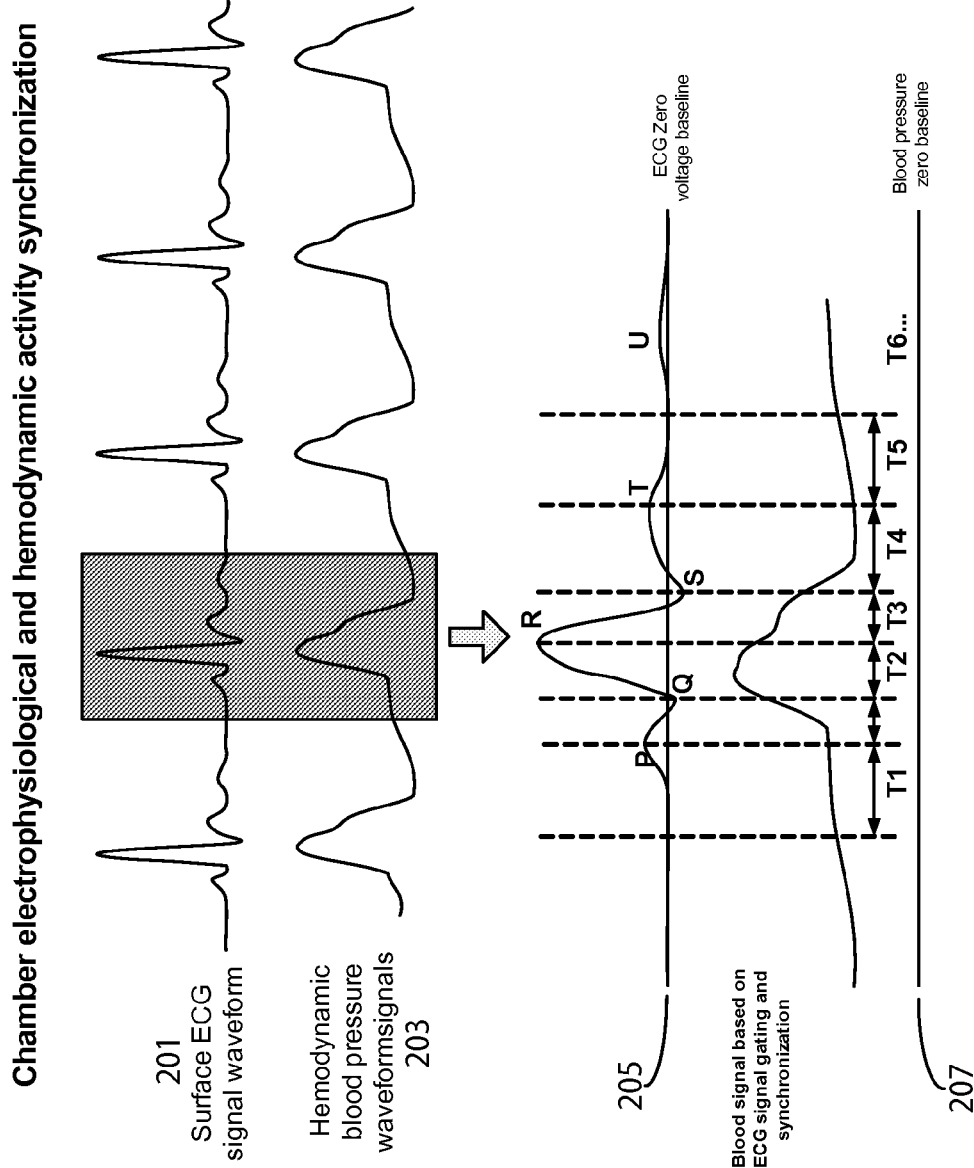
FIG. 2 shows hemodynamic signal segmentation based on electrophysiological signals for extracting parameters associated with function of different cardiac chambers, according to invention principles.

FIG. 2 shows hemodynamic signal segmentation based on electrophysiological signals for extracting parameters associated with function of different cardiac chambers. System 10 derives parameters including, chamber blood output and blood output ratios and compares the parameters of different chambers. System 10 performs a hemodynamic parameter comparison of different heart chambers for tracking chamber and cardiac tissue pathology and also performs a single chamber hemodynamic parameter comparison at different times (e.g. before and after a procedure) and in different phases. Signal processor 15 segments hemodynamic signal 203 (such as a non-invasive blood pressure signal) into sections: T1 to T6 (and late heart activity section T7) as shown in a single cycle waveform 207. Processor 15 uses ECG signal 201 and ECG waves and points (such as P wave, QRS wave, for example) in a single ECG heart cycle (e.g. cycle 205) in segmenting blood pressure waveform cycle 207 into sections T1-T7. Processor 15 uses known ECG signal morphology (P wave, QRS wave, T wave, U wave, for example) in identifying sections T1-T7 and in determining parameters of individual sections T1-T7 including blood pressure parameters, SPO2 signal parameters, dP/dt, blood flow speed and a frequency related parameter, for example, synchronized with cardiac chamber electrophysiological activities. Processor 15 uses electrophysiological signal 201 for hemodynamic signal and waveform segmentation, synchronization and registration and facilitates accurate capture and characterization of hemodynamic signal morphology changes, especially for different chamber hemodynamic activities.

Processor 15 uses different methods to perform hemodynamic signal and waveform segmentation for different purposes including for, systolic and diastolic procedure tracking and maximum blood pressure estimation, for example. In one embodiment, a hemodynamic signal waveform is not segmented and separated using the hemodynamic signal waveform characteristics, but rather is segmented and categorized using a concurrently acquired electrophysiological signal from the same patient. Individual atrial and ventricular heart chamber output is analyzed by segmenting a hemodynamic signal (including an invasive blood pressure signal, SPO2 oxygen signal and capnograph signal) and by calculating a composite parameter indicative of the chamber blood output (such as blood volume, energy, flow, oxygen consumption, for example) and comparison between the chambers. Processor 15 uses the calculated parameters to characterize cardiac pathology including arrhythmias and tissue malfunctions, such as early stage cardiac arrest and acute cardiac ischemia. The system employs hemodynamic signal and vital sign signal segmentation based on electrophysiological signals rather than R wave or other wave synchronization based signal timing analysis.

Figure 3:
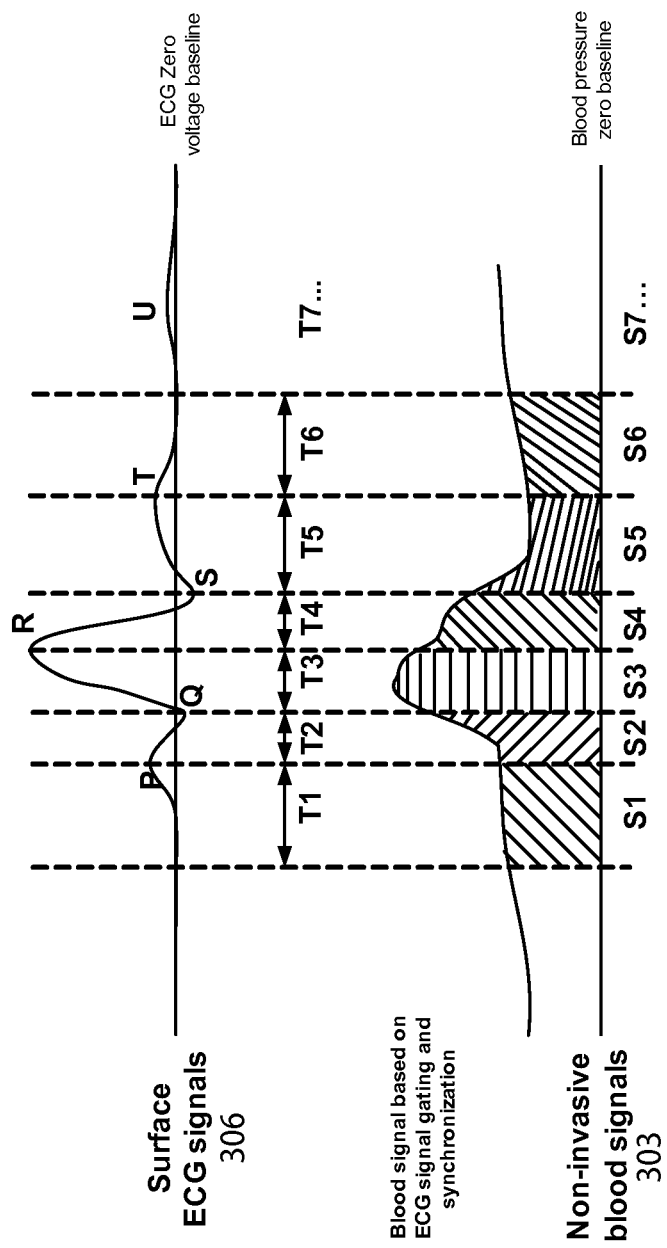
FIG. 3 shows determination of parameters for cardiac function tracking and monitoring, according to invention principles.

FIG. 3 shows determination of parameters for cardiac function tracking and monitoring. Processor 15 adaptively selects and calculates different parameters for different chambers including using a mutual atrial-ventricular blood flow ratio for early detection of myocardial ischemia, for example, in response to user preference and data identifying a clinical application concerned. Hemodynamic waveform 303 over a heart cycle shows advantageous definitions of chamber associated hemodynamic signal parameters S1-S6. Hemodynamic signal 303 is synchronized with P, Q, R, S, T and U waves and points of electrophysiological (ECG) signal 306 associated with a chamber function operational sequence of a heart cycle, such as T1 to T6 indicating atrial to ventricular chamber response timing and duration. Correspondingly, in the blood pressure waveform, S1 to S6 are advantageously defined parameters representing blood volume and flow amount for each timing process and duration. Processor 15 uses ECG function signal gating to categorize and compare hemodynamic signal properties of different heart chambers for early detection of cardiac tissue malfunction and arrhythmia detection.

FIG. 4 shows a Table describing segmented hemodynamic signal portions T1-T6 identified in column 403 and illustrated in (ECG) signal 306 (FIG. 3) associated with a chamber function operational sequence of a heart cycle. The cardiac functions associated with hemodynamic signal portions T1-T6 are identified in column 405 and their associated corresponding time interval segments are defined in column 407. FIG. 5 shows a Table describing segmented signal areas S1-S6 identified in column 503 and illustrated in hemodynamic signal 303 (FIG. 3). Column 505 describes a cardiac function and heart chamber corresponding to associated segmented signal areas S1-S6.

Processor 15 advantageously uses volume and energy index $S_i$, $$S_i = \sum_{i \in T_i} x_i \cdot \Delta t$$

where, $x_i$ is the amplitude of a hemodynamic signal waveform within a particular segment area, such as $i \in T_i$ indicating integration of the data points within segment Ti to derive a volume and energy index Si value. In an embodiment, processor 15 calculates different chamber blood output parameters and ratios for a hemodynamic signal. These parameters and ratios are used for detection, characterization and prediction of early cardiac arrhythmia, severity, location, trend, a treatment time sequence and priority, for example.

FIG. 6 shows a Table showing calculated parameters for chamber output and arrhythmia diagnosis. Specifically, column 603 shows different parameters and ratios calculated by processor 15 for a hemodynamic signal and column 605 indicates their corresponding associated cardiac functions. The hemodynamic signal comprises an invasive or noninvasive blood pressure signal, an SPO2 signal, capnograph, or blood related or vital sign signal. The hemodynamic ratios and parameters of column 603 are combined for diagnosis of cardiac rhythm and tissue malfunction using hemodynamic chamber ratio, $$\text{Hemo\_combined\_ratio} = \sum_{m \in any\_of\_hemo\_Ratios} \alpha_m \text{Hemo\_Ratio}_m$$

where Hemo_Ratio$_m$ comprises a Hemo_Ratio, including atrial hemodynamic cross chamber ratios, ventricular cross chamber hemodynamic ratios and mutual chamber blood output ratios as shown in column 603 (FIG. 6); $\alpha_m$ is a weighting parameter for a combination of different hemodynamic ratios. The parameter m (number of hemodynamic ratios combined) is determined by a user or the system based on data identifying a clinical application or procedure, for example.

The hemodynamic chamber ratio and parameter values and their distribution (such as mean value, standard deviation, for example) of a patient may vary over time. The system characterizes a statistical pattern within a cardiac chamber blood output ratio distribution using a parameter variation determination function. A sequentially calculated variation value and an associated probability characterization is used for severity, type, timing, abnormal trend determination and treatment priority determination, for example. Statistical calculations are performed for a sequential parameter series of hemodynamic chamber blood output or ratio values, for S1, for example and a shifting window (size is automatically determined in response to analysis sensitivity and noise within a data series and here a 10 data point window is used, for example). For each window, the mean value mean(S1), standard deviation STD(S1), variation and variability are calculated by using the following functions.

$$\text{Mean or averaging value (expectation): mean}(X) = \frac{1}{N} \sum_{i \in N} X(i);$$

$$\text{Standard deviation: } STD(X) = \frac{1}{N-1} \sum_{i \in N-1} (X(i) - \text{mean}(X))$$

$$\text{Signal Variation} = \frac{\text{mean}(X)}{STD(X)}$$

$$\text{Signal Variability} = \frac{\max(X - \text{mean}(X))}{\text{mean}(X)}$$

The calculated statistical values are used for detecting and characterizing a blood pressure signal pattern. In one embodiment the system improves reliability and sensitivity analysis and severity analysis, of cardiac condition detection using a hypothesis test and statistical analysis, such as a student test or multi-way sequential hypothesis test, for example. The system is used in non-invasive hemodynamic diagnosis for cardiac arrhythmia detection and characterization. A derived statistical parameter, such as variation or variability of hemodynamic chamber output associated calculated values facilitates detection of emerging cardiac abnormality as well as characterization of severity of a calculated hemodynamic value and a trend in cardiac pathology, for example.

Figure 7:
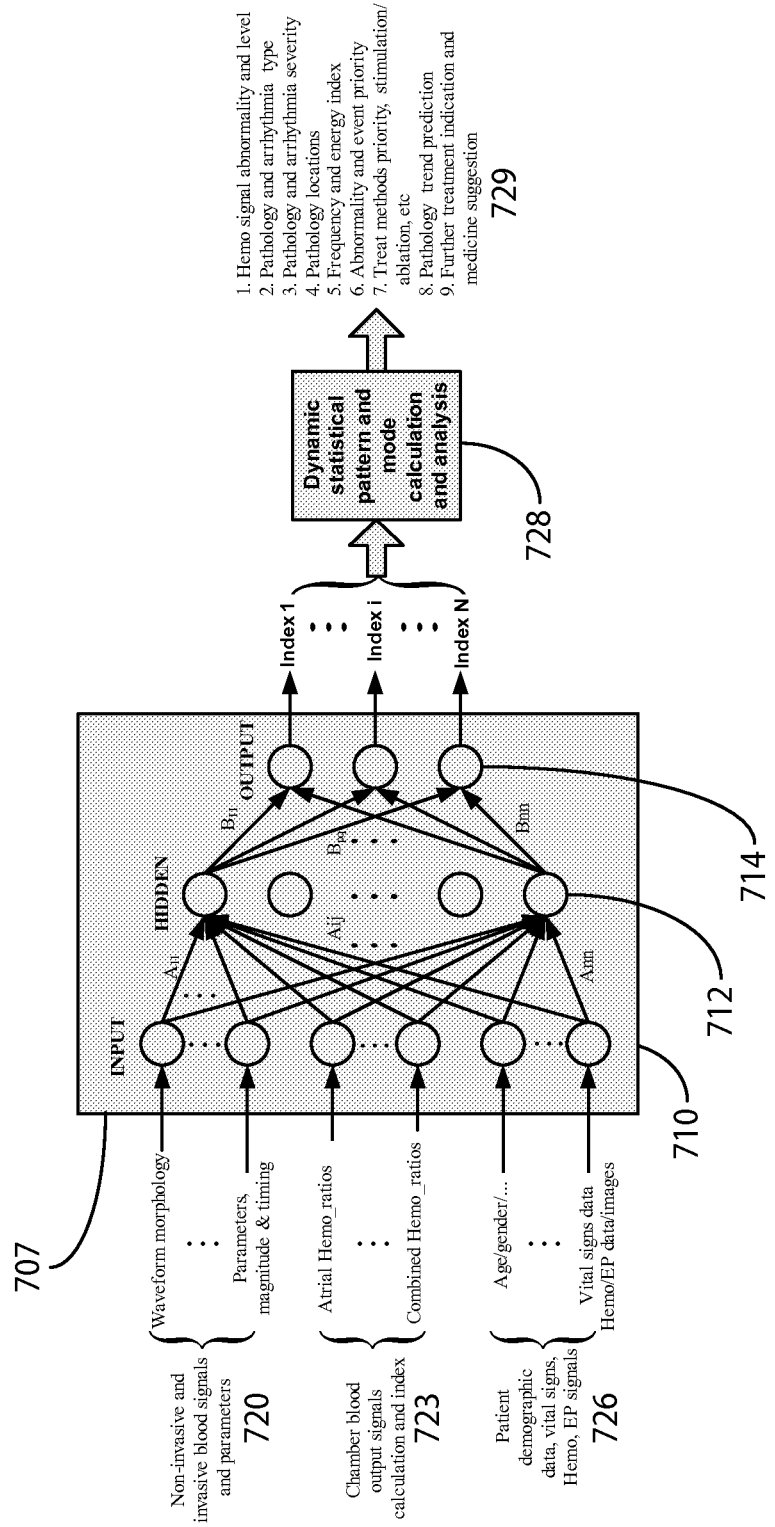
FIG. 7 shows an artificial neural network (ANN) for heart performance characterization and abnormality detection, according to invention principles.

FIG. 7 shows artificial neural network (ANN) 707 for heart performance characterization and abnormality detection. Different systems such as an artificial neural network, expert system and fuzzy model system, for example are usable to combine multiple parameters for identifying hemodynamic characteristics. An artificial neural network (ANN) in one embodiment is utilized for integration and nonlinear combination of multiple kinds of patient information and calculated results. ANN unit 707 performs hemodynamic non-invasive chamber blood output determination and patient health status detection.

ANN unit 707 combines and maps input parameters 720, 723 and 726, to parameters processed by calculation unit 728 that provides output parameters 729. The output parameters 729 indicate atrial arrhythmia position, type, severity and relative priority for treatment, calculated ratios, pathology trend and suggested treatment and medication. ANN unit 707 structure comprises 3 layers, an input layer 710, hidden layer 712 and output layer 714. ANN unit $A_{ij}$ weights are applied between input layer 710 and hidden layer 712 components of the ANN computation and $B_{pq}$ weights are applied between hidden layer 712 and calculation components 714 of the ANN computation. The $A_{ij}$ weights and $B_{pq}$ weights are adaptively adjusted and tuned using a training data set. ANN unit 707 incorporates a self-learning function that processes signals 720, 723 and 726 to increase the accuracy of calculated results.

ANN unit 707 maps input signals 720, 723 and 726 to parameters used by calculation unit 728 to provide a candidate diagnosis or treatment suggestion 729 to localize tissue impairment within an organ and determine time of occurrence within a heart cycle. Input 720 comprises non-invasive blood pressure related signals and hemodynamic parameters derived therefrom, input 723 comprises calculated heart chamber ratios and input 726 comprises patient demographic data (age, weight, height, gender), vitals sign signals, hemodynamic and ECG signals. Output 729 comprises data identifying hemodynamic signal parameters, pathology and arrhythmia type, abnormality location, a frequency and energy parameter, severity of abnormality, effectiveness of an ablation sequence and priorities for treatment. ANN unit 707 combines signal analysis previously described and unit 728 provides pattern calculation to provide quantitative and qualitative results and evaluation of patent health status.

Figure 8:
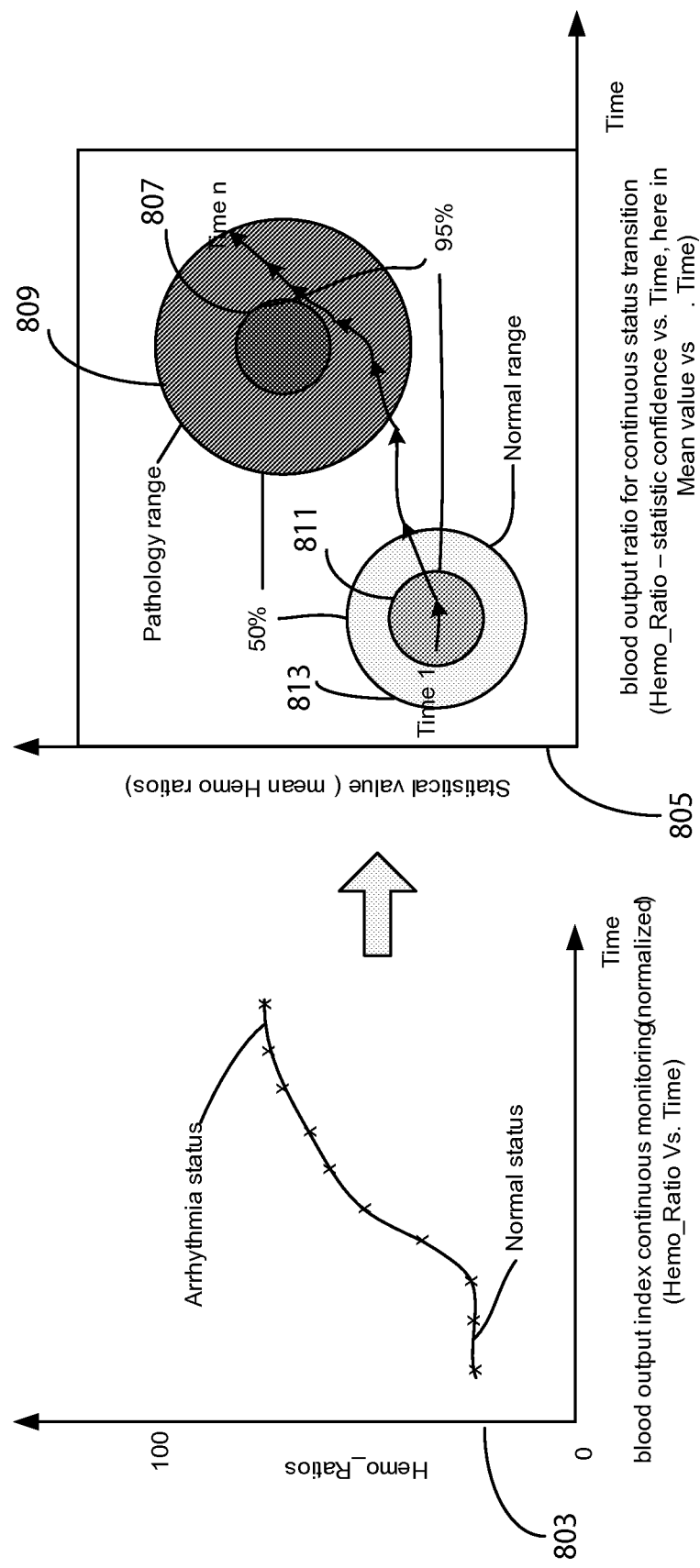
FIG. 8 shows a hemodynamic chamber output ratio graph and real time monitoring representation, according to invention principles.

The hemodynamic chamber blood output estimation and ratio calculations are used for cardiac tissue monitoring. FIG. 8 shows a hemodynamic chamber output ratio graph and real time graphical monitoring representation provided by processor 15. Graph 803 shows a single dimensional hemodynamic ratio value over time indicating value changes from normal to pathology with the higher value of the hemodynamic ratio indicating increasing likelihood of arrhythmia. Graph 805 shows a continuously calculated mean value of a hemodynamic ratio parameter over time together with statistical confidence thresholds such as 50% and 95% thresholds indicating cardiac rhythm transition from a first status comprising a first heart rhythm at time 1 to a second status comprising a second heart rhythm at time n. This graphical representation may be utilized for hemodynamic chamber blood output pattern change detection. Graph 805 may alternatively show a continuously calculated standard deviation or hypothesis test value over time. The different size of circles 807, 809, 811 and 813 indicate different statistical confidence limits e.g. if a mean value of the hemodynamic ratio is within circle 811 there is a 95% confidence level that the value is normal and if the mean value is outside circle 811 but within circle 813, there is a 50% confidence level that the value is normal. If a mean value of the hemodynamic ratio is within circle 807 there is a 95% confidence level that the value is abnormal and if the mean value is outside circle 807 but within circle 809, there is a 50% confidence level that the value is abnormal.

Figure 9:
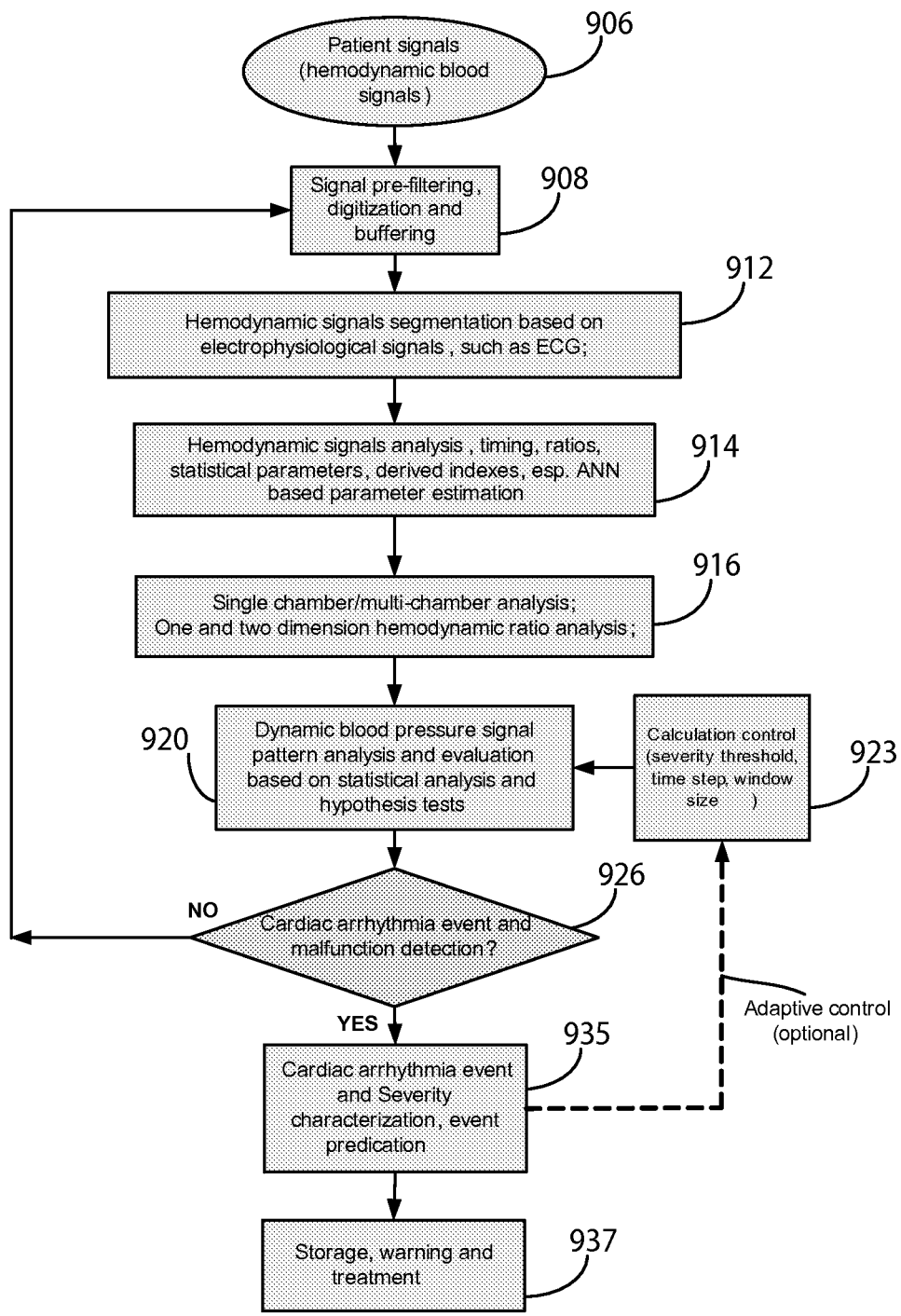
FIG. 9 shows a flowchart of a method for monitoring and characterizing cardiac function and activity status based on hemodynamic chamber output ratio analysis, according to invention principles.

FIG. 9 shows a flowchart of a method for monitoring and characterizing cardiac function and activity status based on hemodynamic chamber output ratio analysis. Signal processor 15 buffers, filters (to remove power line noise, patient movement and respiration noise) and digitizes a hemodynamic blood flow related signal (a non-invasive blood pressure signal, SPO2 signal, blood volume signal, or a calculated blood pressure related parameter) and an ECG signal in step 908 received from a patient in step 906. Processor 15 in step 908 filters the received signal data using a filter adaptively selected in response to data indicating clinical application to remove patient movement and respiratory artifacts as well as power line noise. In step 912, processor 15 segments the filtered hemodynamic signal into portions using signal points and portions of the received ECG signal. The ECG signal portions include P wave, Q wave, R wave, S wave, T wave, U wave portions. In another embodiment, processor 15 uses another type of electrophysiological signal.

The P wave, Q wave, R wave, S wave, T wave, U wave portions and points of the received ECG signal are identified by detecting peaks within the received ECG data using a known peak detector and by segmenting the ECG signal into windows where the waves are expected and by identifying the peaks within the windows. The start point of a wave, for example, is identified by a variety of known different methods. In one method a wave start point comprises where the signal crosses a baseline of the signal (in a predetermined wave window, for example). Alternatively, a wave start point may comprise a peak or valley of signal. The baseline of the signal may comprise a zero voltage line if a static (DC) voltage signal component is filtered out from the signal. The signal processor includes a timing detector for determining time duration between the signal peaks and valleys. The time detector uses a clock counter for counting a clock between the peak and valley points and the counting is initiated and terminated in response to the detected peak and valley characteristics.

In one embodiment, signal processor 15 detects blood pressure waveform segments T1-T6 within a received blood pressure waveform by synchronization of a heart electrical activity waveform and peak and valley detection of ECG wave P, Q, R, S, T, U segments using a known peak and valley detector and by identifying peaks of other waves by segmenting the signal represented by the sampled data into windows where the waves are expected and identifying the peaks within the windows. The Start point of a P wave, for example, is identified by a variety of known different methods. In one method the P wave start point comprises where the signal crosses a baseline of the signal (in a predetermined P wave window, for example). The baseline of the signal may comprise a zero voltage line if a static (DC) voltage signal component is filtered out from the signal.

In step 914, processor 15 performs hemodynamic chamber blood signal analysis and calculates hemodynamic timing and output ratios as well as statistical parameters by determining standard deviation, variability and variation, derived parameters as previously described and ANN derived parameters. Signal processor 15 in step 916 performs single chamber hemodynamic ratio and cross chamber hemodynamic ratio analysis and multi-chamber mutual ratio analysis. Processor 15 in step 920 performs statistical analysis on calculated hemodynamic blood pressure parameters. If signal processor 15 in step 926, identifies a medical condition based on the calculated hemodynamic parameters such as an atrial arrhythmia condition or event or another abnormality, processor 15 characterizes the condition in step 935. Processor 15 identifies and characterizes the condition using predetermined mapping information, associating ranges of the calculated parameters or values derived from the calculated parameters with corresponding medical conditions, and compares the calculated parameters or values derived from the calculated parameters, with the ranges and generates an alert message indicating a potential medical condition. The predetermined mapping information associates ranges of the calculated parameters or value derived from the calculated parameters with particular patient demographic characteristics and with corresponding medical conditions and the signal processor uses patient demographic data including at least one of, age weight, gender and height in comparing the calculated parameters or values derived from the calculated parameters with the ranges and generating an alert message indicating a potential medical condition.

In step 937 processor 15 generates an alert message indicating a potential medical condition and stores data indicating the identified condition and associated calculated parameters in repository 17. The warning threshold is pre-determined and adaptively controlled. Processor 15 in step 923 adaptively adjusts a time window for chamber blood ratio and parameter analysis and in response to blood pressure signal quality, such as noise level. The system may be utilized not only with invasive and non-invasive blood pressure signals, but also other blood related signal data, such as SPO2 signals. The hemodynamic chamber blood output ratio analysis is utilized to monitor and diagnose different kinds of clinical events and cardiac pathology within a heart, such as atrial fibrillation, atrial flutter, ventricle arrhythmias, for example.

Figure 10:
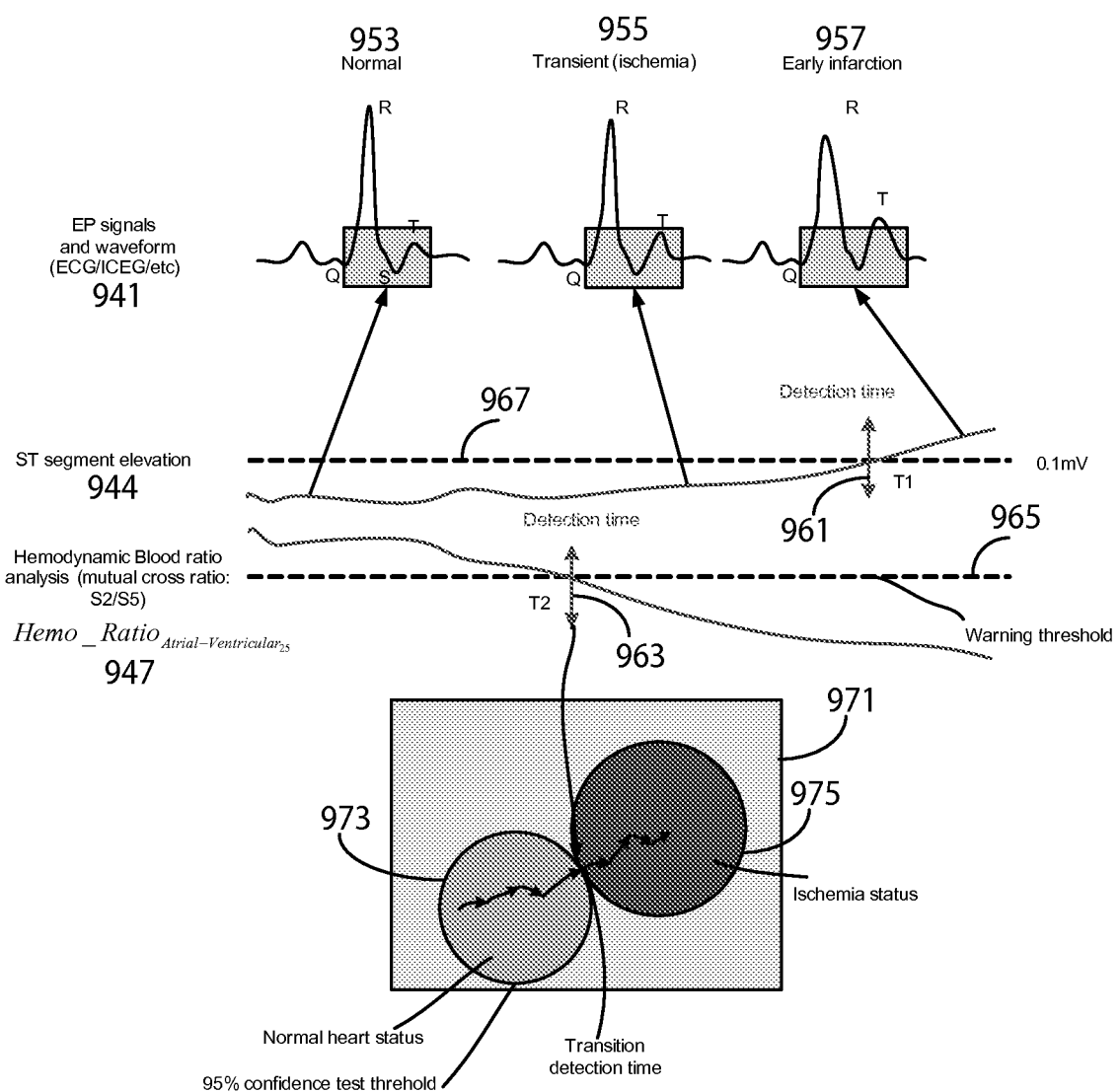
FIG. 10 illustrates myocardial ischemia event and activity analysis based on hemodynamic chamber blood output ratio analysis and characterization, according to invention principles.
Figure 11:
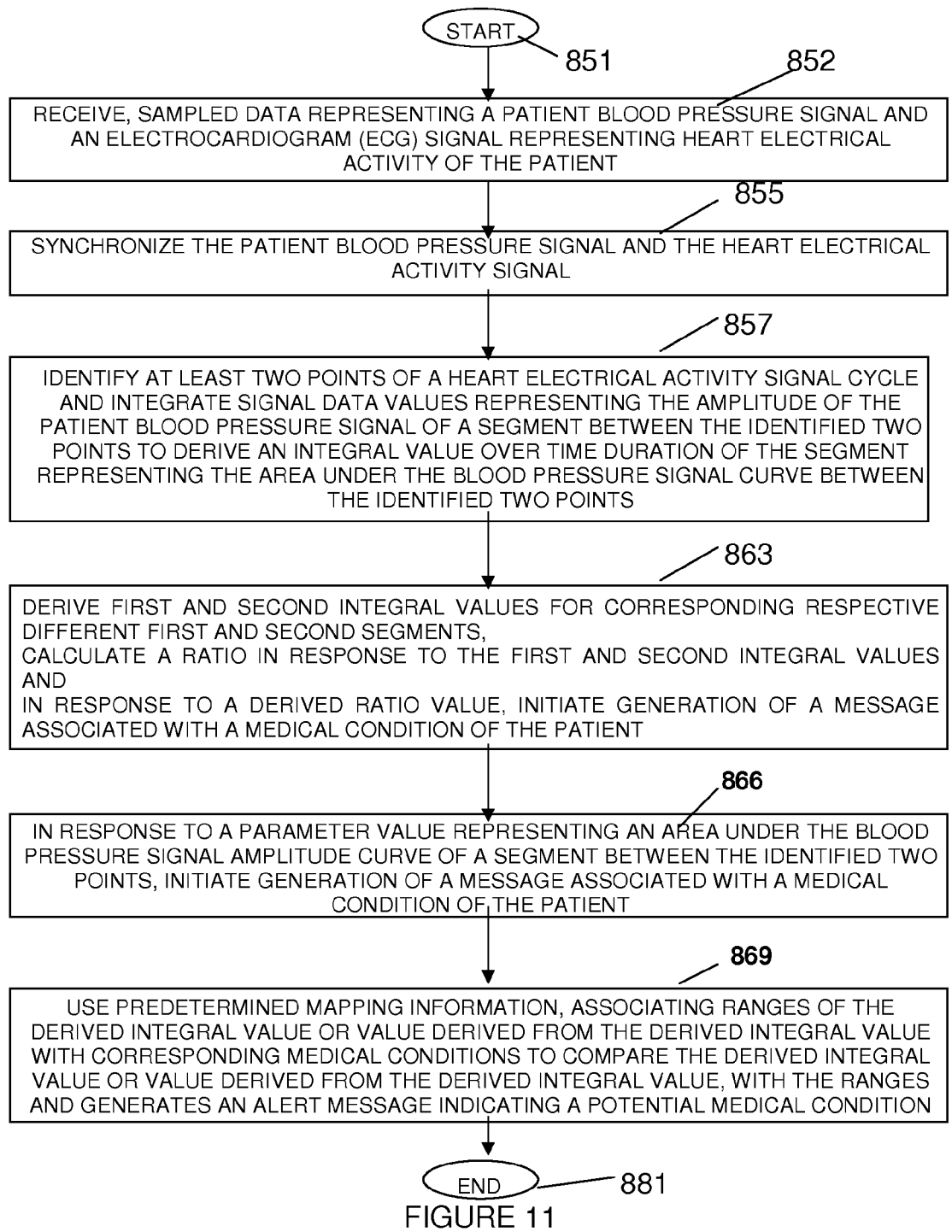
FIG. 11 shows a flowchart of a process used by a system for heart performance characterization and abnormality detection, according to invention principles.

FIG. 10 illustrates myocardial ischemia event and activity analysis based on hemodynamic chamber blood output ratio analysis and characterization. The hemodynamic ratio analysis in one embodiment uses atrial to ventricular mutual ratios for early stage myocardial ischemia, and infarction detection and characterization. Normal 953, transient ischemic 955 and early infarction 957 episodes of ECG signal 941 that are shown for comparison of different cardiac status. An ECG signal ST segment value is plotted in waveform 944 and compared against a 0.1 mV elevation threshold 967. The ST segment elevation indicates a myocardial ischemia event at time T1 961 while the hemodynamic blood ratio analysis plot 947 (a mutual blood ratio between volume and energy portions S2 to S5) detects a myocardial event at time T2 963 by comparison with predetermined threshold 965, approximately 10 seconds earlier. In one embodiment, the warning threshold is determined by hypothesis test, with statistical confidence 95%. Further, a hemodynamic ratio is continuously calculated and plotted in real time in graph 971. First circle 973 shows a region with 95% confidence level indicating a normal parameter value and second circle 975 shows a region with 95% confidence level indicating an abnormal parameter value indicating ischemia. Processor 15 changes detection threshold 965 to detect acute small changes within a hemodynamic waveform FIG. 11 shows a flowchart of a process used by system 10 (FIG. 1) for heart performance characterization and abnormality detection. In step 852 following the start at step 851, input processor 20 receives, sampled data representing a patient blood pressure signal and a concurrently acquired electrocardiogram (ECG) signal representing heart electrical activity of the patient. In step 855 at least one signal processor 15, synchronizes the patient blood pressure signal and the heart electrical activity signal. Processor 15 in step 857 identifies at least two points of a heart electrical activity signal cycle and integrates signal data values representing the amplitude of the patient blood pressure signal of a segment between the identified two points to derive an integral value over time duration of the segment representing the area under the blood pressure signal waveform between the identified two points.

The identified at least two points of a heart electrical activity signal cycle, comprise at least two points of P, Q, R, S, T and U points and the identified two points are substantially from the onset (zero voltage) of atrial depolarization to the peak of a P wave, corresponding to an atrial blood injection period. In different embodiments, the identified two points are, (a) substantially from peak of a P wave to the peak valley of a Q wave corresponding to repolarization of atrial chamber activity, (b) substantially from peak of a Q wave to the peak of an R wave corresponding to ventricular chamber depolarization activity, (c) substantially from peak of an R wave to the peak of an S wave corresponding to late ventricular chamber depolarization activity, (d) substantially from peak of an S wave to the peak of a T wave corresponding to repolarization of the ventricular chamber activity and (e) substantially from peak of a T wave to the end (zero voltage) of the T wave corresponding to late ventricular chamber repolarization activity.

In step 863, processor 15 derives first and second integral values for corresponding respective different first and second segments, calculates a ratio in response to the first and second integral values and in response to a derived ratio value, initiates generation of a message associated with a medical condition of the patient. The different first and second segments comprise at least one of, (a) both atrial associated segments, (b) both ventricular associated segments and (c) an atrial associated segment and a ventricular associated segment respectively. In step 866, processor 15 in response to a parameter value representing an area under the blood pressure signal amplitude waveform of a segment between the identified two points, initiates generation of a message associated with a medical condition of the patient. Signal processor 15 provides a value derived from the derived integral value by determining a standard deviation or variance of the derived integral value and by determining a standard deviation or variance of a ratio derived using derived integral values.

Signal processor 15 in step 869 uses predetermined mapping information, associating ranges of the derived integral value or value derived from the derived integral value with corresponding medical conditions, and compares the derived integral value or value derived from the derived integral value, with the ranges and generates an alert message indicating a potential medical condition. The predetermined mapping information associates ranges of the derived integral value or values derived from the derived integral value with particular patient demographic characteristics and with corresponding medical conditions. The signal processor uses patient demographic data including at least one of, age weight, gender and height in comparing the derived integral value or value derived from the derived integral value with the ranges and generates an alert message indicating a potential medical condition. In one embodiment, the signal processor uses predetermined mapping information, associating a threshold value with the derived integral value or values derived from the derived integral value with corresponding medical conditions, and compares the derived integral value or values derived from the derived integral value, with the threshold value and generates an alert message indicating a potential medical condition. The process of FIG. 11 terminates at step 869.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor.

The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-11 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system acquires and categorizes hemodynamic signals of a patient associated with different heart chambers and derives a chamber based blood output ratio and related parameters for early stage myocardial ischemia detection by synchronized segmentation of the hemodynamic signals based on a corresponding concurrently acquired ECG signal from the patient. Further, the processes and applications may, in alternative embodiments, be located on one or more (e.g., distributed) processing devices on a network linking the units FIG. 1. Any of the functions and steps provided in FIGS. 1-11 may be implemented in hardware, software or a combination of both. No claim element herein is to be construed under the provisions of 35 U.S.C. 112, sixth paragraph, unless the element is expressly recited using the phrase "means for."

What is claimed is:

1. A system for heart performance characterization and cardiac arrhythmia detection, comprising:
an input processor configured to receive:
sampled data representing a patient blood pressure signal associated with a patient, and
a concurrently acquired electrocardiogram (ECG) signal representing heart electrical activity of said patient; and
at least one signal processor configured to:
synchronize said patient blood pressure signal and the ECG signal,
identify a first set of points of the ECG signal based on one or more morphological characteristics of the ECG signal,
define a first segment of the patient blood pressure signal based on the first set of points,
derive a first integral value representing an area under a first signal amplitude waveform associated with the first segment,
identify a second set of points of the ECG signal based on the one or more morphological characteristics of the ECG signal,
define a second segment of the patient blood pressure signal based on the second set of points,
derive a second integral value representing an area under a second signal amplitude waveform associated with the second segment,
calculating a ratio of the first integral value and the second integral value;

identify a potential cardiac arrhythmia based on said ratio of the first integral value and the second integral value, and generate an alert message indicating the potential cardiac arrhythmia.

2. A system according to claim 1, wherein
the identified first set of points of the ECG signal, comprise at least two points of P, Q, R, S, T and U points and
said identified first set of points are substantially from onset (zero voltage) of atrial depolarization to peak of a P wave, corresponding to an atrial blood injection period.

3. A system according to claim 1, wherein
said identified first set of points are substantially from peak of a P wave to the peak valley of a Q wave corresponding to repolarization of atrial chamber activity.

4. A system according to claim 1,
wherein said identified first set of points are substantially from peak of a Q wave to the peak of an R wave corresponding to ventricular chamber depolarization activity.

5. A system according to claim 1, wherein
said identified first set of points are substantially from peak of an R wave to the peak of an S wave corresponding to late ventricular chamber depolarization activity.

6. A system according to claim 1,
wherein said identified first set of points are substantially from peak of an S wave to the peak of a T wave corresponding to repolarization of ventricular chamber activity.

7. A system according to claim 1,
wherein said identified first set of points are substantially from peak of a T wave to the end (zero voltage) of the T wave corresponding to late ventricular chamber repolarization activity.

8. A system according to claim 1, wherein
said first and second segments are at least one of, (a) both atrial associated segments and (b) both ventricular associated segments.

9. A system according to claim 1, wherein
said first and second segments comprise an atrial associated segment and a ventricular associated segment, respectively.

10. A system according to claim 1, wherein
said at least one signal processor is further configured to retrieve predetermined mapping information associating ranges of said ratio of the first integral value and the second integral value with corresponding medical conditions, wherein said at least one signal processor identifies the potential cardiac arrhythmia based on said ratio of the first integral value and the second integral value by comparing said ratio of the first integral value and the second integral value with said ranges in the predetermined mapping information.

11. A system according to claim 10, wherein
said predetermined mapping information associates ranges of said ratio of the first integral value and the second integral value with particular patient demographic characteristics and with the corresponding medical conditions and said at least one signal processor uses patient demographic data including at least one of age, weight, gender and height in comparing said ratio of the first integral value and the second integral value with said ranges.

12. A system according to claim 1, wherein
said at least one signal processor is further configured to:
retrieve predetermined mapping information, associating a threshold value with said ratio of the first integral value and the second integral value with corresponding medical conditions, wherein said at least one signal processor identifies the potential cardiac arrhythmia based on said ratio of the first integral value and the second integral value with said threshold value.

13. A system according to claim 1, wherein
said at least one signal processor provides a value derived from said ratio of the first integral value and the second integral value by determining a standard deviation or variance of said ratio of the first integral value and the second integral value.

14. A system according to claim 1, wherein
said at least one signal processor provides a value derived from said ratio of the first integral value and the second integral value by determining a standard deviation or variance of a ratio derived using said ratio of the first integral value and the second integral value.

15. A method for heart performance characterization and cardiac arrhythmia detection, the method comprising:
receiving,
sampled data representing a patient blood pressure signal associated with a patient, and
a concurrently acquired electrocardiogram (ECG) signal representing heart electrical activity of said patient;
synchronizing said patient blood pressure signal and the ECG signal;
identifying a plurality of segments of the patient blood pressure signal based on one or more morphological characteristics of the ECG signal;
deriving a plurality of integral values, each respective integral value representing an area under a signal amplitude waveform associated with one of the plurality of segments of the patient blood pressure signal;
calculating a plurality of ratios, each ratio comparing two distinct integral values included in the plurality of integral values;
identifying a potential cardiac arrhythmia based on a summation of the plurality of ratios; and
generating an alert message indicating the potential cardiac arrhythmia.

16. The system of claim 1, wherein the at least one signal processor is further configured to:
derive a third integral value representing an area under a third signal amplitude waveform associated with a third segment of the patient blood pressure signal;
derive a fourth integral value representing an area under a fourth signal amplitude waveform associated with a fourth segment of the patient blood pressure signal;
calculating a ratio of the third integral value and the fourth integral value;
calculating a ratio of the third integral value and the first integral value;
calculating a combined ratio equal to a summation of:
the ratio of the first integral value and the second integral value,
the ratio of the third integral value and the fourth integral value, and
the ratio of the third integral value and the first integral value,
wherein the potential cardiac arrhythmia is further identified based on the combined ratio.

17. The system of claim 16, wherein a weighting parameter is applied to each ratio in the summation.

18. The system of claim 16, wherein:
the first segment and the second segment each correspond to a distinct atrial function section of the patient blood pressure signal, and
the third segment and the fourth segment each correspond to a distinct ventricular function section of the patient blood pressure signal.

\* \* \* \* \*